(12) United States Patent
Murray et al.

(10) Patent No.: US 12,326,395 B2
(45) Date of Patent: Jun. 10, 2025

(54) MATERIAL TEST SUB INCLUDING ONE OR MORE GROOVES OR POCKETS FOR DOWNHOLE ENVIRONMENTAL EXPOSURE

(71) Applicant: Halliburton Energy Services, Inc., Houston, TX (US)

(72) Inventors: Fraser Murray, Singapore (SG); Shanshan Yu, Singapore (SG); Thanh Nam Vu, Singapore (SG)

(73) Assignee: Halliburton Energy Services, Inc., Houston, TX (US)

( * ) Notice: Subject to any disclaimer, the term of this patent is extended or adjusted under 35 U.S.C. 154(b) by 361 days.

(21) Appl. No.: 17/841,363

(22) Filed: Jun. 15, 2022

(65) Prior Publication Data
US 2022/0404249 A1  Dec. 22, 2022

Related U.S. Application Data

(60) Provisional application No. 63/211,973, filed on Jun. 17, 2021.

(51) Int. Cl.
*G01N 17/04* (2006.01)
*E21B 49/00* (2006.01)
(Continued)

(52) U.S. Cl.
CPC ......... *G01N 17/046* (2013.01); *E21B 49/003* (2013.01); *G01N 3/08* (2013.01); *G01N 3/10* (2013.01); *G01N 33/20* (2013.01)

(58) Field of Classification Search
CPC ............. G01N 3/08; G01N 2203/0016; G01N 2203/0017; G01N 2203/0019;
(Continued)

(56) References Cited

U.S. PATENT DOCUMENTS 4,928,760 A * 5/1990 Freitas .................. E21B 47/017
166/902
2011/0277995 A1  11/2011 Wilkinson et al.
(Continued)

FOREIGN PATENT DOCUMENTS

CN  203559897 U  4/2014
CN  205958430 U  2/2017
(Continued)

OTHER PUBLICATIONS

Hamid, S., et al., "A Practical Method of Predicting Chemical Scale Formation in Well Completions," SPE 166673, Asia Pacific Oil & Gas Conference and Exhibition, Oct. 22-24, 2013, 20 pages.

*Primary Examiner* — Nathaniel J Kolb
(74) *Attorney, Agent, or Firm* — Scott Richardson; Parker Justiss, P.C.

(57) ABSTRACT

Provided is a downhole material test sub assembly, a well system including the same, and a method for using the same. The downhole material test sub assembly, in one aspect, includes a flange for coupling to a mandrel, and one or more retainer assemblies coupled to the flange, the one or more retainer assemblies configured to accept a test specimen for running within a wellbore on the mandrel. The downhole material test sub assembly, according to another aspect, includes a mandrel and one or more grooves or pockets located in an outer surface of the mandrel, the one or more grooves or pockets configured to accept a test specimen for running within a wellbore on the mandrel.

29 Claims, 14 Drawing Sheets

(51) Int. Cl.
*G01N 3/08* (2006.01)
*G01N 3/10* (2006.01)
*G01N 33/20* (2019.01)

(58) Field of Classification Search
CPC ...... G01N 17/046; G01N 33/20; G01N 33/44; G01N 33/442; G01N 33/445; G01M 13/005; E21B 41/02; E21B 47/00; E21B 47/01; E21B 47/006; E21B 49/00; E21B 49/003; E21B 49/08; E21B 49/082
See application file for complete search history.

(56) References Cited

U.S. PATENT DOCUMENTS

| | | |
|---|---|---|
| 2014/0239168 A1 | 8/2014 | Wang et al. |
| 2017/0030190 A1* | 2/2017 | Serres .................. G01N 3/00 |
| 2018/0024044 A1 | 1/2018 | Ringgenberg et al. |
| 2019/0056305 A1 | 2/2019 | AlJanabi et al. |
| 2019/0242808 A1 | 8/2019 | Chen et al. |
| 2019/0249540 A1* | 8/2019 | Ito ........................ E21B 47/00 |
| 2022/0235647 A1* | 7/2022 | Haque .................. E21B 47/006 |

FOREIGN PATENT DOCUMENTS

| | | |
|---|---|---|
| CN | 209416883 U | 9/2019 |
| WO | 2021007182 A1 | 1/2021 |

* cited by examiner

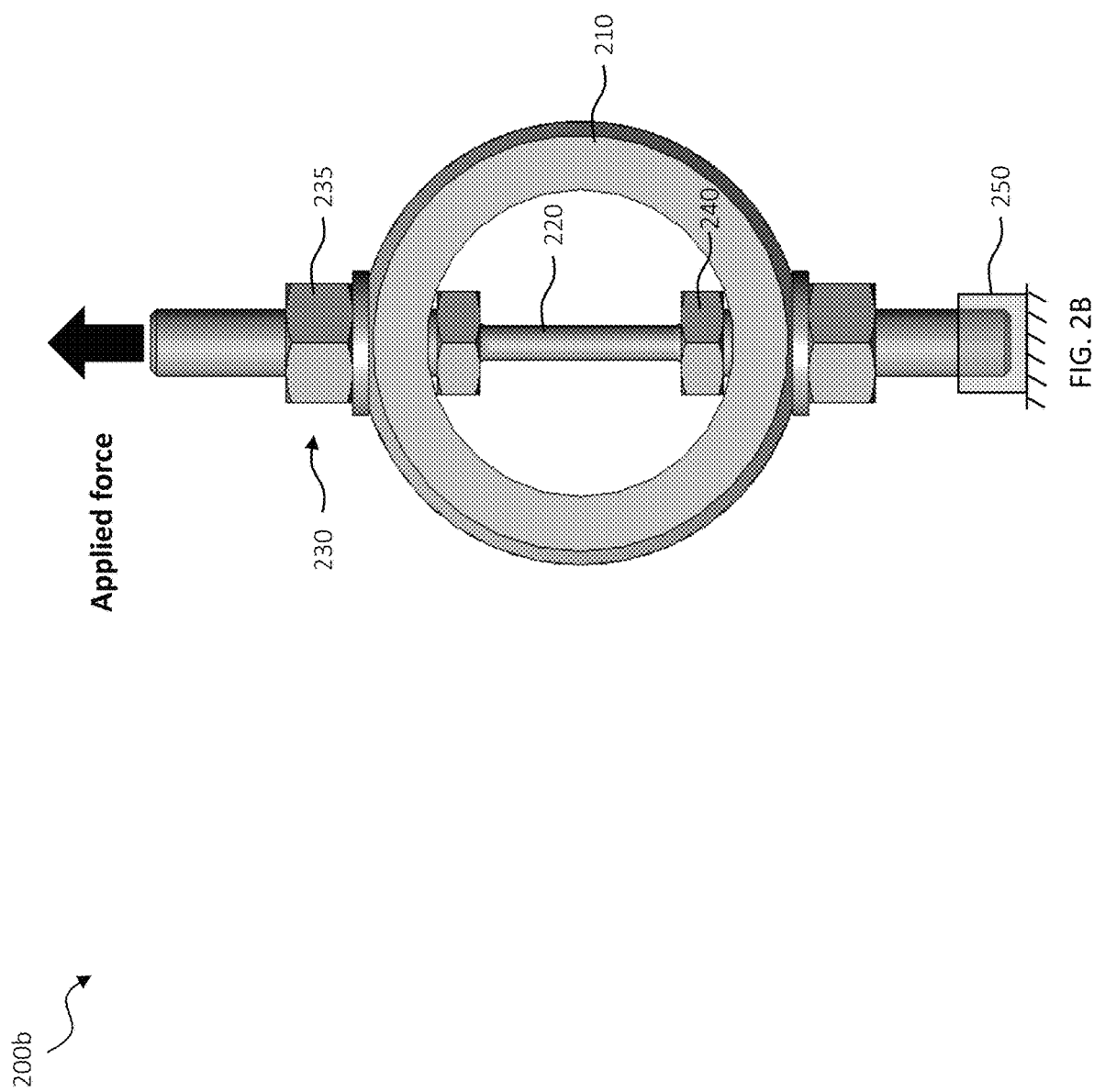

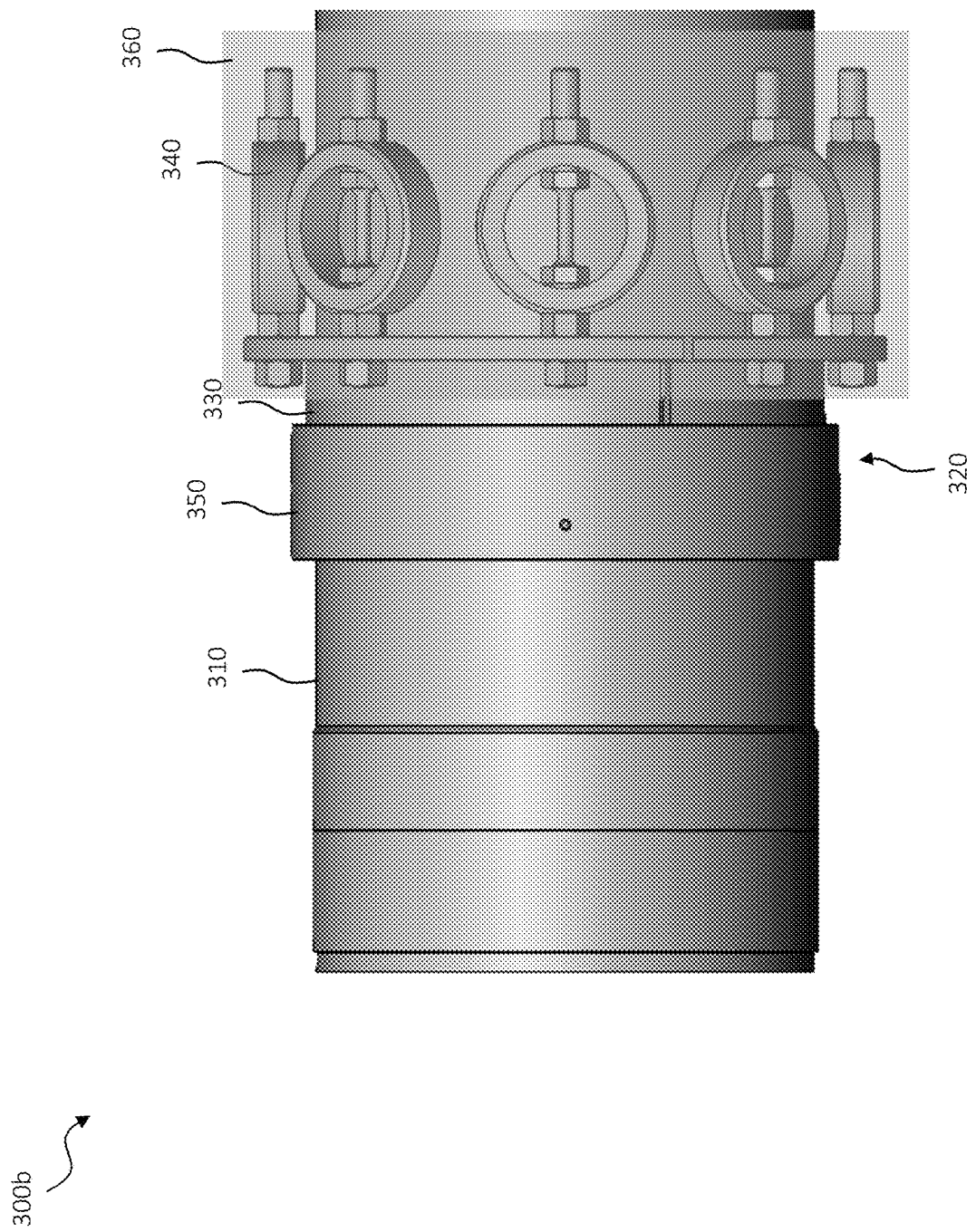

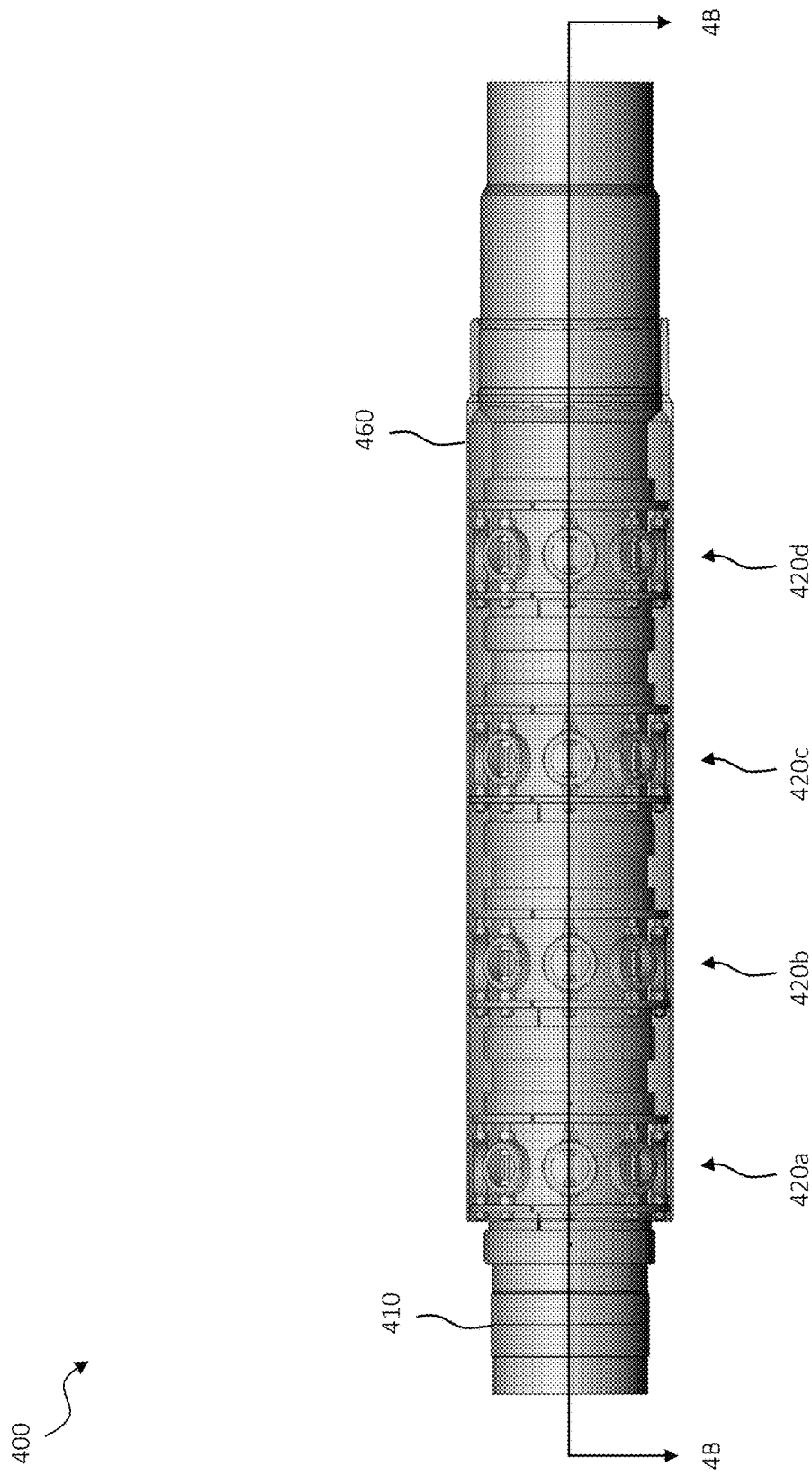

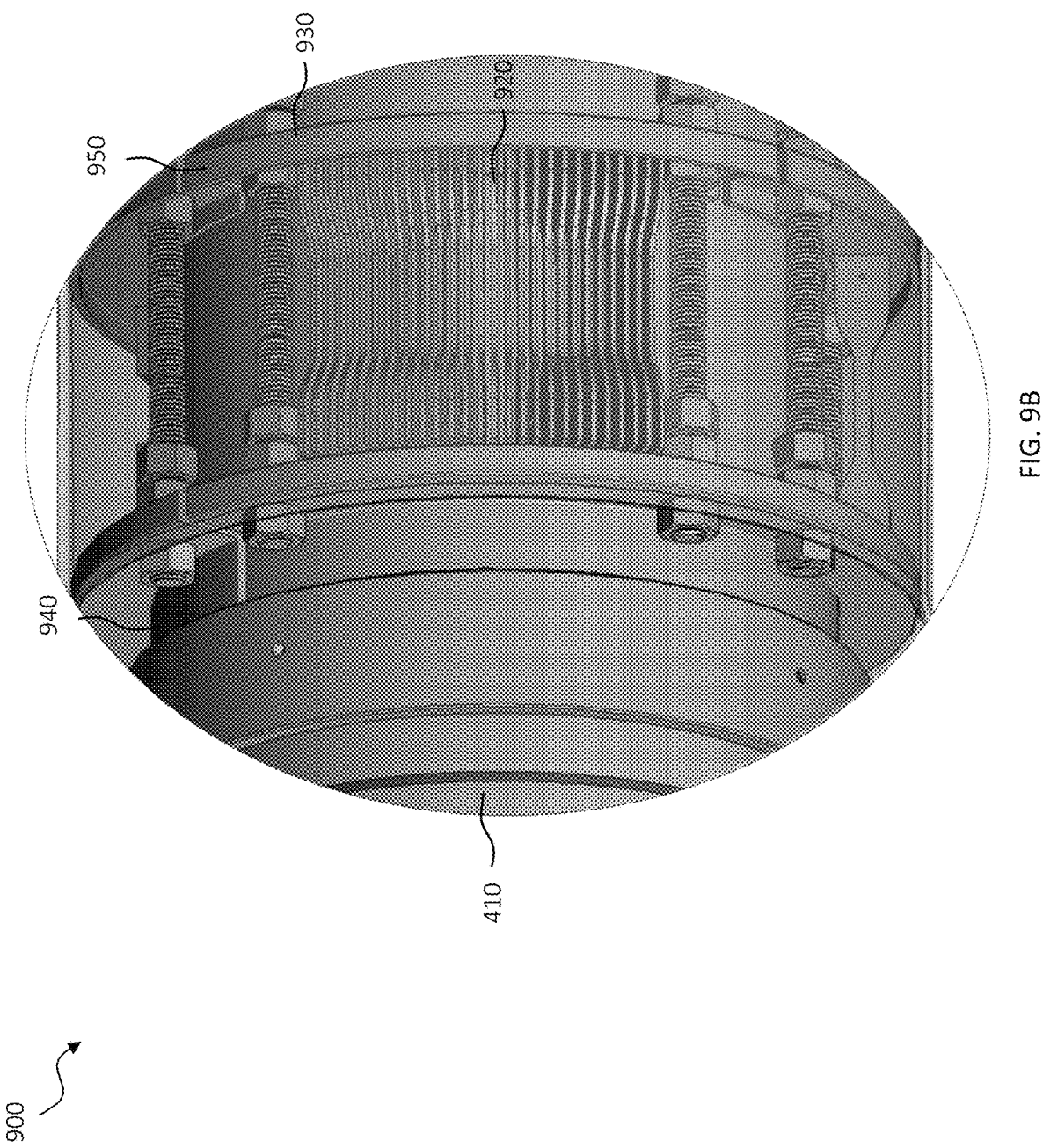

MATERIAL TEST SUB INCLUDING ONE OR MORE GROOVES OR POCKETS FOR DOWNHOLE ENVIRONMENTAL EXPOSURE

CROSS-REFERENCE TO RELATED APPLICATION

This application claims the benefit of U.S. Provisional Application Ser. No. 63/211,973, filed on Jun. 17, 2021, entitled "MATERIAL TEST SUB FOR DOWNHOLE ENVIRONMENTAL EXPOSURE," commonly assigned with this application and incorporated herein by reference in its entirety.

BACKGROUND

As companies become more engaged in the energy transition, they are asked to adapt their equipment for use in new downhole environments and applications which include $H_2$ storage and $CO_2$ injection. A knowledge gap exists in the field of material science on how the materials commonly used in completion tool design will perform in these new environments. This knowledge gap can be closed through lab-based testing; however, it is extremely costly and time consuming to test multiple different materials in environments that represent downhole conditions.

BRIEF DESCRIPTION

Reference is now made to the following descriptions taken in conjunction with the accompanying drawings, in which:

FIGS. 2A and 2B illustrate a retainer ring assembly according to one or more embodiments of the disclosure;

FIGS. 3A and 3B illustrate a material test sub designed, manufactured, and operated according to one or more embodiments of the disclosure;

FIGS. 4A and 4B illustrate a material test sub designed, manufactured, and operated according to one or more embodiments of the disclosure;

FIGS. 9A and 9B illustrate a material test sub designed, manufactured, and operated according to one or more other embodiments of the disclosure.

DETAILED DESCRIPTION

Figure 1:
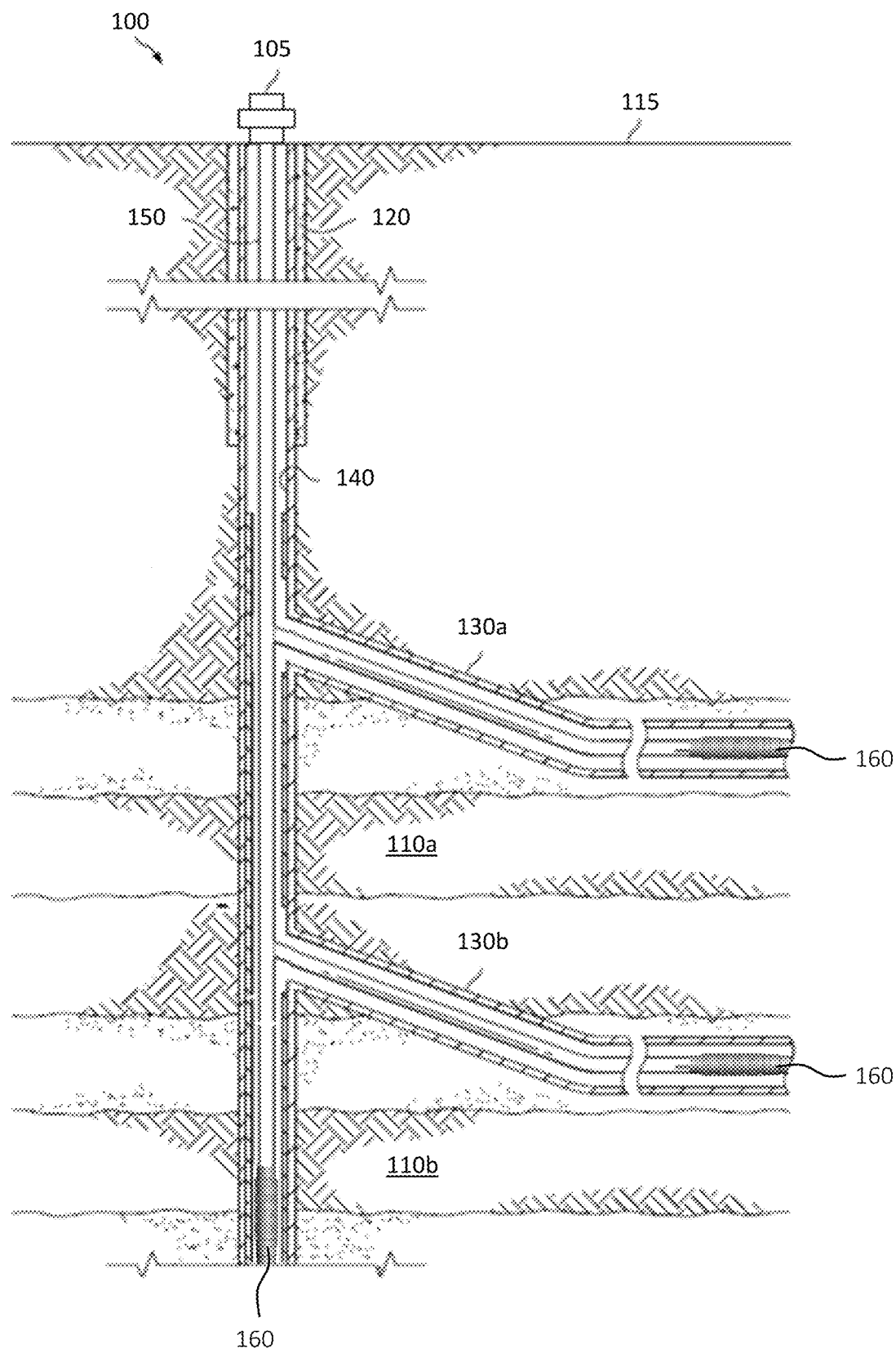
FIG. 1 illustrates a schematic view of a well system according to one or more embodiments of the disclosure.

The present disclosure has recognized that some environmental conditions, such as concentration of impurities, are given in range form due to uncertainty, which drives testing at worst case conditions generating overly conservative results. Based, at least in part, on the foregoing, the present disclosure has developed a system and/or method that allows an unlimited number of material samples to be carried downhole and exposed to actual environmental conditions. Performing material testing in this way is advantageous from both commercial and accuracy perspectives. Although initially targeting new energy applications, this system and/or method can also be used in traditional oil and gas applications, including high-pressure and/or high-temperature (HPHT) applications.

One solution of the present disclosure is a downhole material test sub (MTS), which allows an array of metallic and/or non-metallic material samples to be conveyed downhole as part of the completion. The solution allows material test specimens (e.g., metallic test specimens) to be accurately pre-stressed in either tension or compression, such that the combined effect of stress and environmental exposure can be understood. The material test sub also allows elastomeric and plastic test specimens to be carried downhole (e.g., either in the form of dumbbell material samples or in traditional O-ring groove geometry, among others). Furthermore, if conveyance as part of the completion string is not possible, the system and/or method can also be adapted for thru-tubing installation below either a bridge plug or lock mandrel. Furthermore, in one or more embodiments, the design is modular, and thus provides flexibility in terms of sample carrying capacity.

Accordingly, a solution according to the present disclosure removes environmental testing from the expensive lab-based setting. Additionally, a solution according to the present disclosure also utilizes a unique pre-stressing feature, which allows test specimens to be loaded in either tension or compression during exposure to downhole conditions. Furthermore, a solution according to the present disclosure removes the need to perform expensive lab based environmental testing to advance one's knowledge in the field of material science. The data collected from a system and/or method according to the present disclosure will allow future optimization in material selection, with a view to reducing the overall cost of goods sold and providing an opportunity to enhance one's gross profit.

Provided, in at least one embodiment, is a downhole material test sub concept, which is configured to carry an array of metallic and/or non-metallic material test specimens downhole. The material test sub, in at least one embodiment, can be run as part of the completion string, with one known placement (e.g., among many different placements) below the production packer. For example, in at least one embodiment, the material test sub will be positioned below the retrievable production packer and conveyed as part of the completion string tailpipe, with the intention of exposing all material samples to the conditions present in the downhole environment. In at least one embodiment, the material test sub will be recovered as part of the completion string, allowing the material test specimens to be collected and sent to a lab for analysis. The analysis, in one embodiment, will identify how different materials perform in the downhole environment, with this data serving many purposes including future optimization in material selection.

The material test sub is initially targeted towards a hydrogen ($H_2$) storage environment, where little is known about the performance of materials commonly used in completion tool design. However, the material test sub could also be used in many different well environments, including carbon dioxide ($CO_2$) injection, as well as traditional oil and gas applications. In circumstances where it is not feasible to convey the material test sub as part of the completion string, it can again be adapted for thru tubing use where it could be installed below a retrievable bridge plug set in the tubing, or a lock mandrel set in a landing nipple.

There are several advantages to this concept over traditional lab-based testing. First, a user of the present system and/or method can expose the material test specimens to actual downhole conditions, instead of making assumptions based on approximations or possible ranges and errors in supplied parameters. Second, the system of the present disclosure may be designed in a modular fashion, which provides a limitless capability in terms of test material sample quantity. Third, only a handful of labs offer environmental testing, and it is usually extremely costly. This system and/or method can be deployed in almost any well environment to negate lab based environmental testing with only the material test sub cost to bear. Fourth, material test specimens according to the present disclosure can be accurately pre-loaded in tension and compression so the combined effects of environmental exposure and stress level can be determined.

In at least one embodiment, the material test sub will be conveyed with the completion string and will have a maximum OD and minimum ID that is aligned to the geometry of the production packer or production tubing. The desire, in one embodiment, is to install the material test sub as part of the tailpipe, below the production packer to ensure exposure to the well conditions. Placing the material test sub here also alleviates concerns with failure of the system, as such an event would not create an integrity issue for the completion. A thru-tubing version of the material test sub could be a scaled down version of the traditional system, sized to ensure successful conveyance into the well. The material test sub, in certain embodiments, will carry an array of circumferentially mounted metallic tensile test specimens that are pre-loaded in tension or compression to various stress levels.

FIG. 1 illustrates a schematic view of a well system 100 according to one or more embodiments of the disclosure. The well system 100 includes a wellhead 105 positioned over one or more oil and gas formations 110a, 110b located below the earth's surface 115. Although a land-based wellhead 105 is illustrated in FIG. 1, the scope of this disclosure is not thereby limited, and thus could potentially apply to offshore applications. The teachings of this disclosure may also be applied to other land-based oil and gas systems and/or offshore oil and gas systems different from that illustrated.

As shown, a main wellbore 120 has been drilled through the various earth strata, including the subterranean formations 110a, 110b. The term "first" wellbore is used herein to designate a wellbore from which another wellbore is drilled. It is to be noted, however, that a first wellbore 120 does not necessarily extend directly to the earth's surface, but could instead be a branch of yet another wellbore. Thus, the first wellbore 120 may be a first main wellbore, or a first lateral wellbore, and remain within the scope of the disclosure. The multilateral well 100 additionally includes one or more lateral wellbores 130a, 130b extending therefrom. The term "lateral" wellbore is used herein to designate a wellbore that is drilled outwardly from its intersection with another wellbore, such as the first wellbore 120. Moreover, a lateral wellbore may have another lateral wellbore drilled outwardly therefrom. While only two lateral wellbores 130a, 130b are illustrated in FIG. 1, certain embodiments may employ more than just two lateral wellbores.

One or more casing strings 140 may be at least partially cemented within the first wellbore 120, and optionally contained within the one or more lateral wellbores 130a, 130b. The term "casing" is used herein to designate a tubular string used to line a wellbore. Casing may be of the type known to those skilled in the art as "liner" and may be made of any material, such as steel or composite material and may be segmented or continuous, such as coiled tubing. A completion string 150 according to the present disclosure may be positioned in the first wellbore 120 and/or the one or more lateral wellbores 130a, 130b. The well system 100 may additionally includes one or more material test sub's 160 designed, manufactured and operated according to the disclosure, as will be discussed below. In the illustrated embodiment, the one or more material test sub's 160 are coupled to the completion string 150.

Figure 2A:
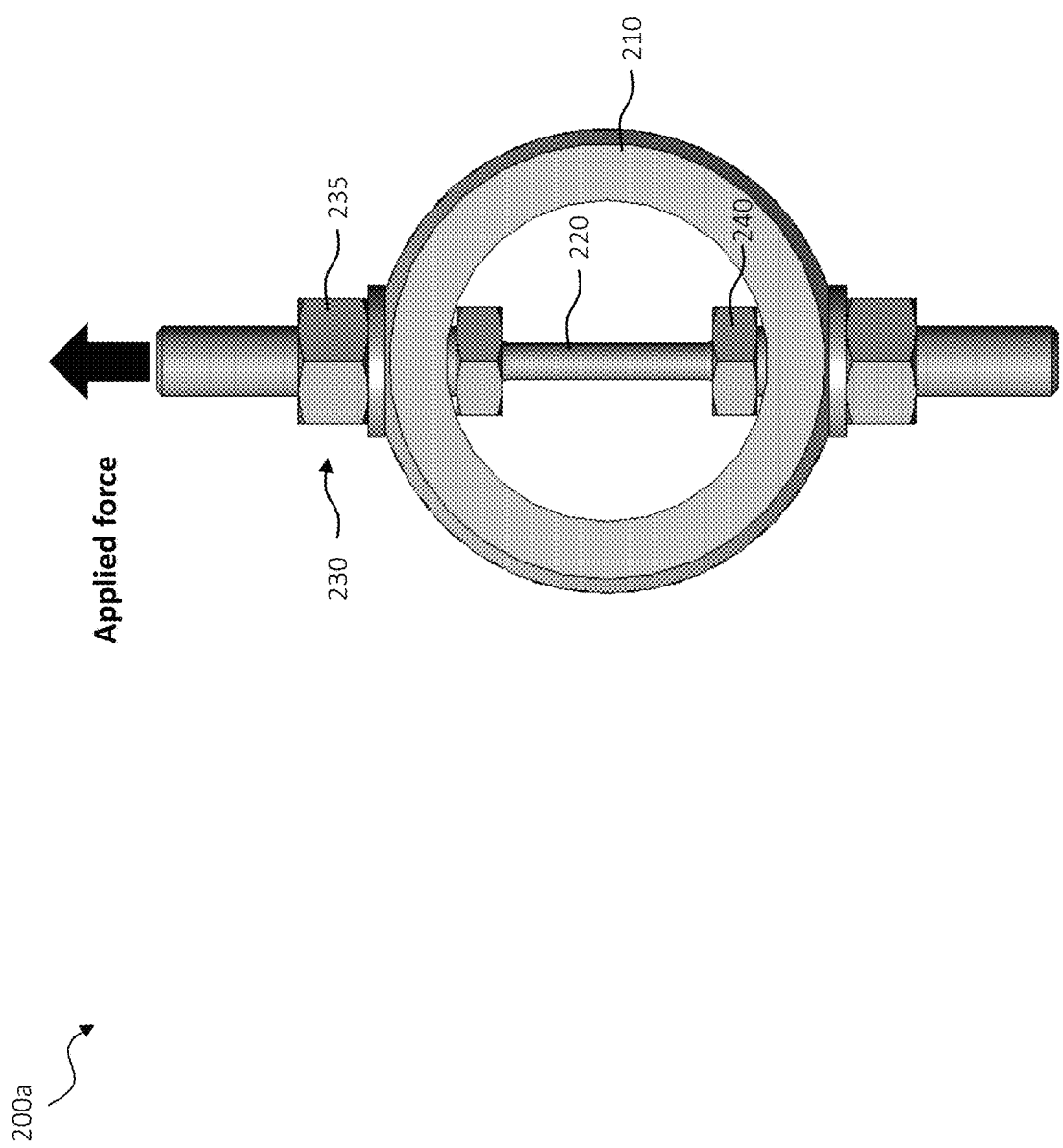

Turning to FIG. 2A, a retainer ring assembly 200a according to one or more embodiments of the disclosure (e.g., a pre-loading mechanism) may be used for a material test sub (e.g., the one or more material test sub's 160 of FIG. 1). In at least one embodiment, the retainer ring assembly 200a may include a retainer ring 210, which in one embodiment may be configured to accept a variety of different material test specimens 220. In at least one embodiment, the retainer ring 210 is configured to accept a standard ASME metallic material test specimen 220 (e.g., with threaded ends), upon which a nut arrangement 230 (e.g., a collection of locking nuts 235 and retainer nuts 240) may be installed. In at least one embodiment, the test specimen 220 is accurately stressed by axially fixing the ring and pulling tension through the material sample using a ram. The tension may be pulled against the nut arrangement 230 on the opposite end of the retainer ring 210 relative to the ram. Once the desired stress level is reached, the nut arrangement 230 on the same end of the material test specimen 220 as the ram is tightened to lock the load in against the retainer ring 210. If the material test specimen 220 breaks into two pieces, the retainer nut 240 may retain the broken material test specimen 220 on the retainer ring 210 to minimize the risk of the material test specimen 220 dropping into the wellbore. After retrieving the material test sub, the broken samples are still attached to the retainer ring for traceability. For a sample pre-loaded in compression, the nut arrangement 230 could include two nuts on the inside of the retainer ring 210 to repeat the same process.

Turning to FIG. 2B, illustrated is a retainer ring assembly 200b according to one or more alternative embodiments of the disclosure. The retainer ring assembly 200b is similar in many respects to the retainer ring assembly 200a of FIG. 2A. Accordingly, like reference numbers have been used to illustrated similar, if not identical, features. The retainer ring assembly 200b differs for the most part from the retainer ring assembly 200b, in that the retainer ring assembly 200b provides tension to the material test specimen 220 by connecting the opposite end of the material test specimen 220 to a fixture 250, so that the tension is pulled against the fixture 250.

Figure 3A:
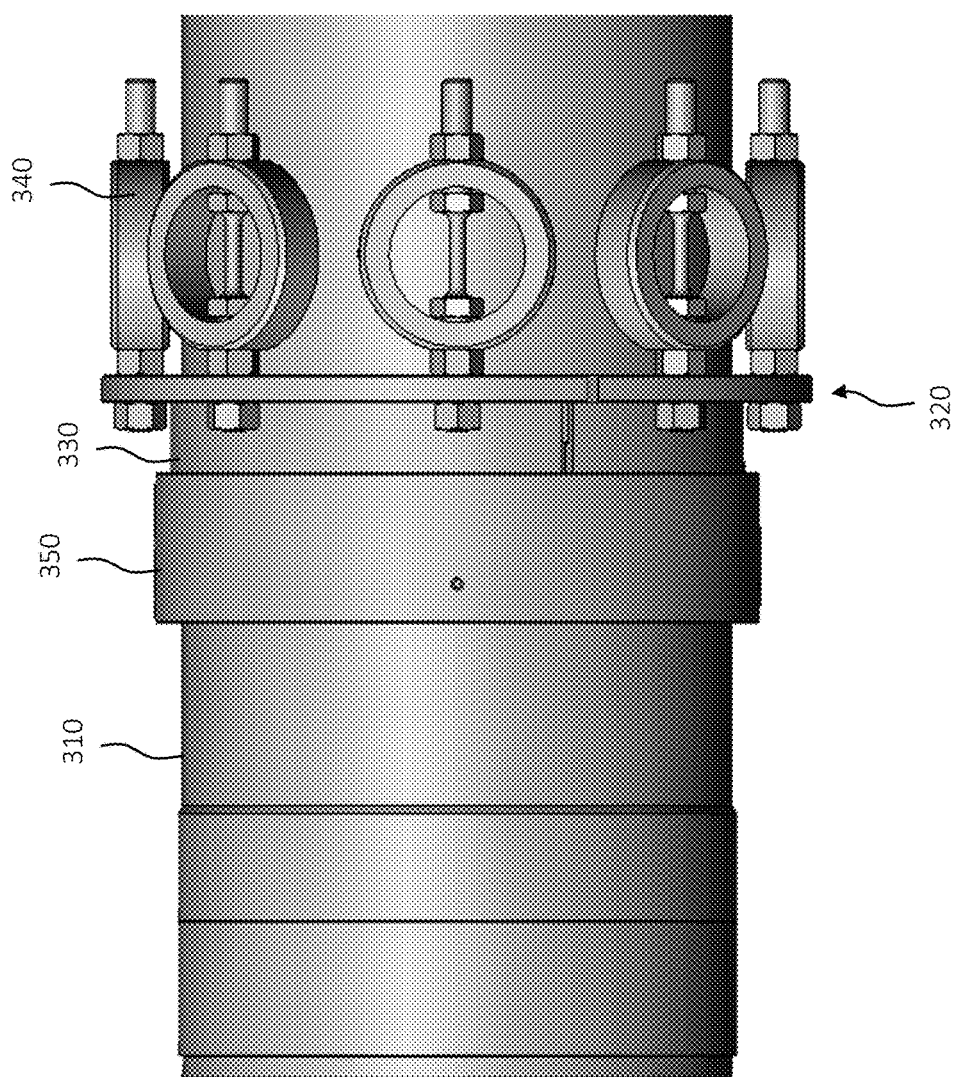

Turning to FIG. 3A, illustrated is a material test sub 300a (e.g., tensile material test sub) designed, manufactured, and operated according to one or more embodiments of the disclosure. In the illustrated embodiment, the material test sub 300a includes a mandrel or tubular 310 having a material test sub assembly (MTSA) 320 positioned thereabout. The material test sub assembly 320, in at least one embodiment, includes a flange 330. Coupled to the flange 330 (e.g., circumferentially mounted on the flange 330), in the illustrated embodiment, are one or more retainer ring assemblies 340 (e.g., similar in certain embodiments to the retainer ring assembly 200 of FIG. 2). In the illustrated embodiment, a flange retainer ring 350 couples the flange 330, and thus the retainer rings 340, to the mandrel or tubular 310.

Turning to FIG. 3B, illustrated is a material test sub 300b (e.g., tensile material test sub) designed, manufactured, and operated according to one or more alternative embodiments of the disclosure. The material test sub 300b of FIG. 3B is similar in many respects to the material test sub 300a of FIG. 3A. Accordingly, like reference numbers have been used to indicate similar, if not identical, features. The material test sub 300b differs, for the most part, from the material test sub 300a, in that the material test sub 300b includes a shroud 360 placed over the test specimens, for example to prevent damage when running in/out of hole and to retain debris from failed material samples. The shroud 360, in at least one embodiment, is configured to move linearly with respect to the mandrel or tubular 310 to expose the test specimens. In at least one other embodiment, the shroud 360 is configured to rotate with respect to the mandrel or tubular 310 to expose the test specimens. In such an embodiment, an opening or slot in the shroud 360 could be used to access the test specimens. With the opening or slot located in the shroud 360, the O-rings or backup rings can be installed into the mandrel or tubular 310 without applying grease. The lack of grease, in this embodiment, allows for maximum exposure of the material test specimen to the wellbore environment. In yet another embodiment, the shroud 360 is configured to move linearly and rotate with respect to the mandrel or tubular 310 to expose the test specimens. In such an embodiment, the shroud 360 and the mandrel or tubular 310 could have a threaded engagement to provide the relative linear and rotational movement.

Figure 4B:
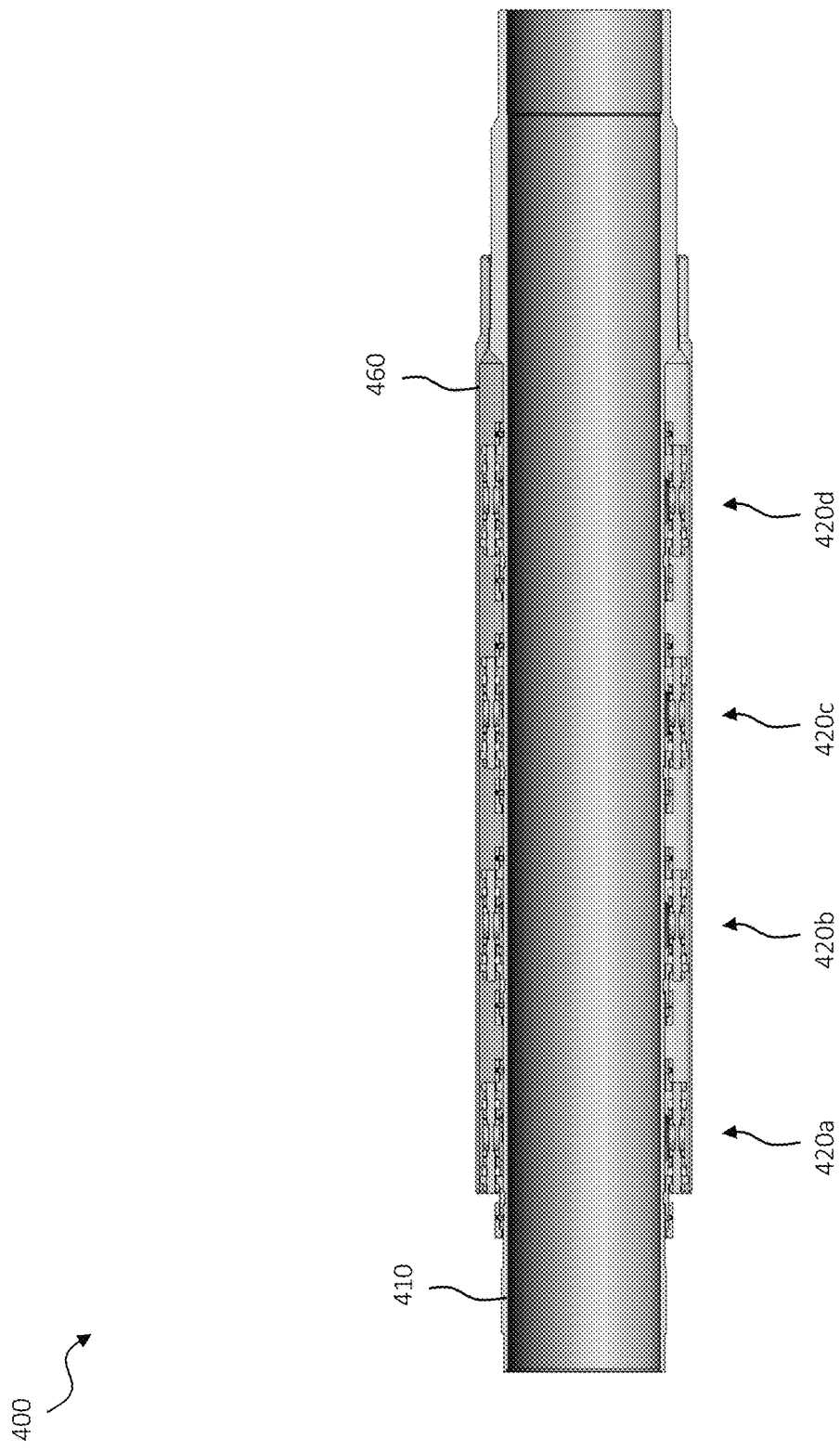

Turning to FIG. 4A, illustrated is a material test sub 400 designed, manufactured and operated according to the present disclosure. As shown, in certain embodiments and depending on the geometry constraints, several material test sub assemblies 420a, 420b, 420c, 420d, etc. (e.g., similar in certain embodiments to the material test sub assembly 320 of FIG. 3A) can be installed on the mandrel or tubular 410 to provide an almost limitless capacity for test specimens. It should be noted that although the individual test specimens can be highly stressed, these loads are isolated to the retainer ring and so are not passed to the mandrel or tubular 410. This serves an important function, as it preserves the integrity of the entire system, particularly in environments where the effects of high stresses on material performance are unknown. The material test sub 400 additionally includes a shroud 460, as discussed above. Turning briefly to FIG. 4B, illustrated is a cross-sectional view of the material test sub 400 of FIG. 4A, taken through the line 4B-4B of FIG. 4A.

Figure 5:
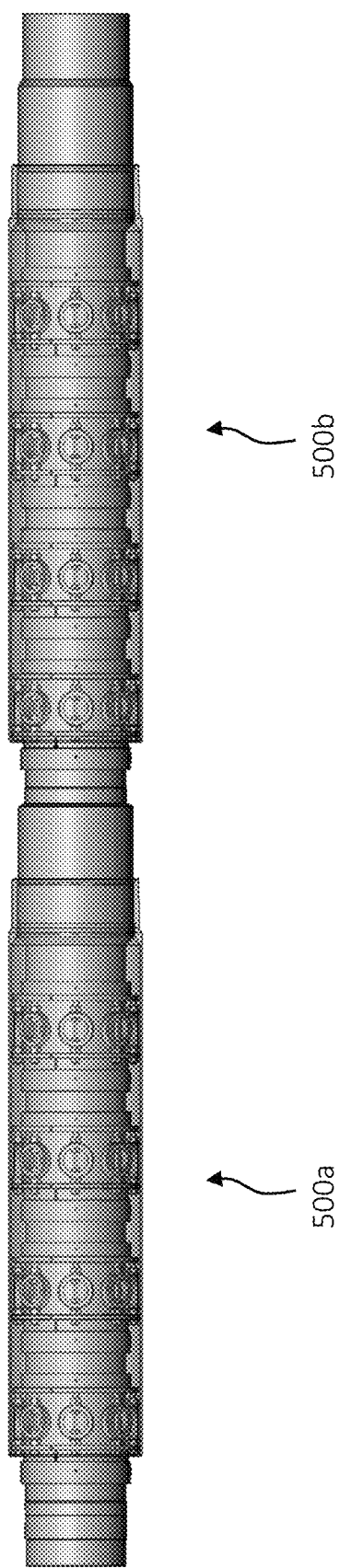
FIG. 5 illustrates an embodiment wherein multiple material test subs are stacked according to the disclosure.

Turning to FIG. 5, illustrated is an embodiment wherein multiple material test subs 500a, 500b . . . 500n are stacked (e.g., modularly, such as in the same plane). While two material test subs 500a, 500b are illustrated in FIG. 5, any number of material test subs 500 may be stacked and remain within the scope of the disclosure.

Figure 6:
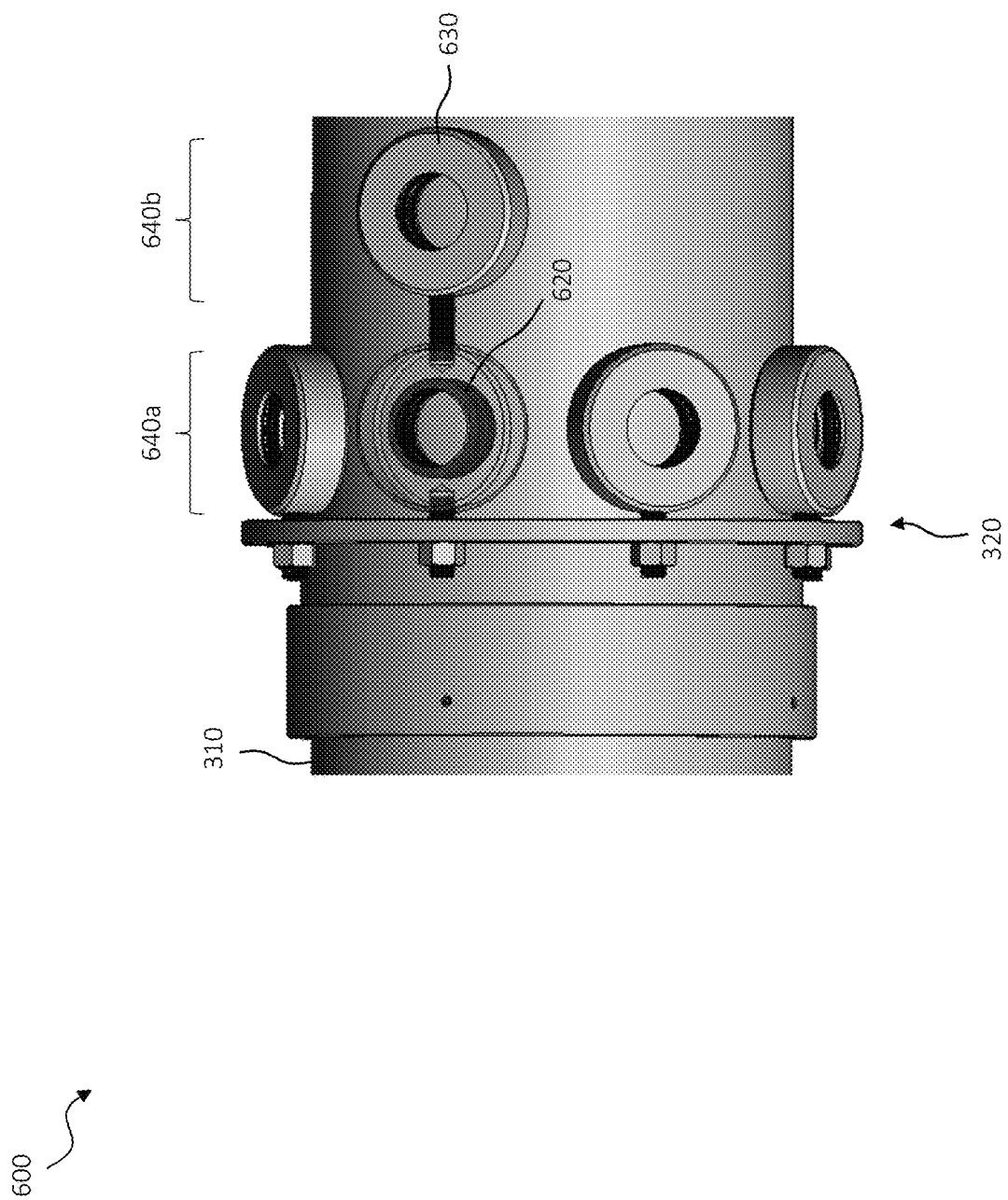
FIG. 6 illustrates a material test sub designed, manufactured, and operated according to one or more other embodiments of the disclosure.

The material test sub can also carry a series of non-metallic materials including O-rings, elastomeric dumbbell samples and back-up rings, among others. Turning to FIG. 6, illustrated is another embodiment of a material test sub 600 designed, manufactured and operated according to one embodiment of the disclosure. The material test sub 600 is similar in certain respects to the material test sub 300a of FIG. 3A. Accordingly, like reference numbers have been used to indicate similar features. The material test sub 600 differs, for the most part, from the material test sub 300a, in that the material test sub 600 employs O-rings and/or backup rings 620 that are carried in sizes grooves within a donut arrangement 630. In the illustrated embodiment, the material test sub 600 includes a first layer 640a of backup rings 620 and a second layer 640b of backup rings 620.

Figure 7A:
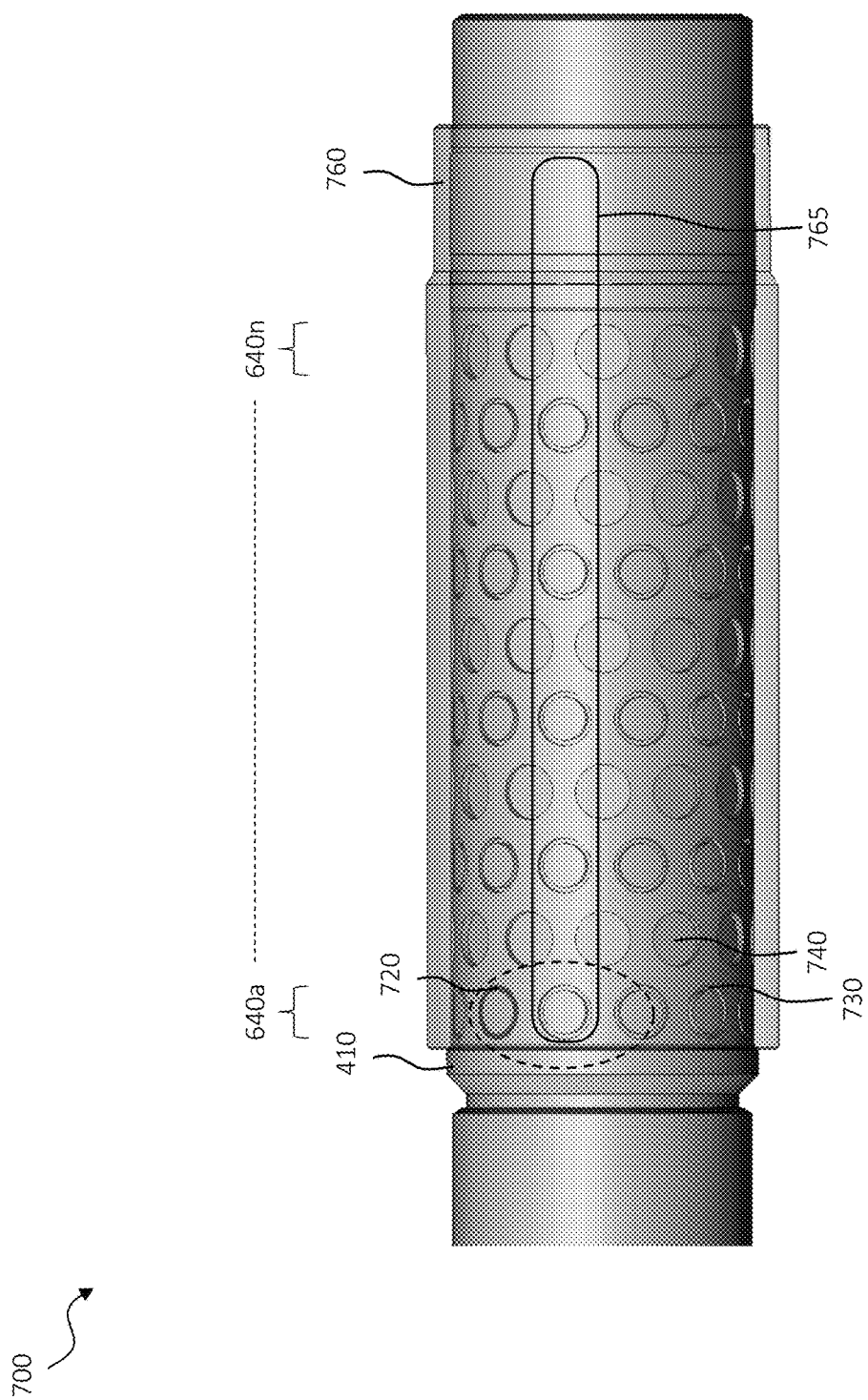
FIGS. 7A and 7B illustrate a material test sub designed, manufactured, and operated according to one or more other embodiments of the disclosure.

Turning to FIG. 7A, illustrated is another embodiment of a material test sub 700 designed, manufactured and operated according to one embodiment of the disclosure. The material test sub 700 is similar in certain respects to the material test sub 400 of FIG. 4A. Accordingly, like reference numbers have been used to indicate similar features. The material test sub 700 differs, for the most part, from the material test sub 400, in that the material test sub 700 employs a series of grooves 730 or pockets 740 within the tubular or mandrel 410, the series of grooves 730 or pockets 740 configured to position one or more O-rings and/or backup rings 720. In at least one embodiment, the series of grooves 730 or pockets 740 are sized to create different stress levels for the O-rings and/or backup rings 720, based upon experimental needs.

In the illustrated embodiment, the material test sub 700 includes multiple layers 750 of grooves 730 or pockets 740 (e.g., layers 750a-750n) located along the mandrel 410. In at least one embodiment, the grooves 730 or pockets 740 in each layer 750 are radially spaced about the mandrel 410. In at least one embodiment, the grooves 730 or pockets 740 in one layer 750 are rotationally offset from the grooves 730 or pockets 740 in an adjacent layer 750.

Figure 7B:
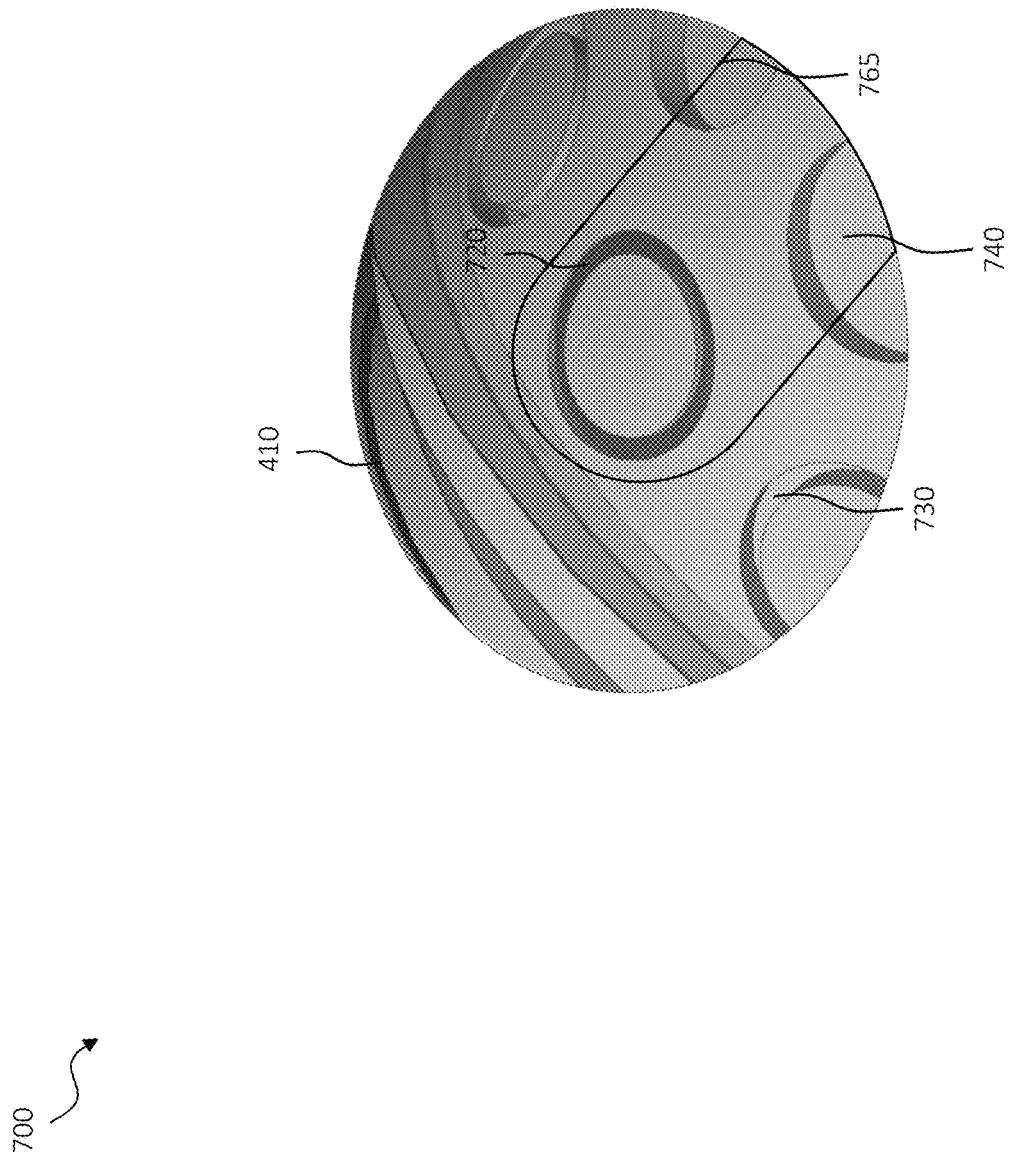

The material test sub 700 may also include a shroud 760 placed over the test specimens, for example to prevent damage when running in/out of hole, retain debris from failed material samples, and keeping the O-rings and/or backup rings 720 in place. The shroud 760, in at least one embodiment, is configured to move linearly with respect to the mandrel or tubular 410 to expose the test specimens. In at least one other embodiment, the shroud 760 is configured to rotate with respect to the mandrel or tubular 410 to expose the test specimens. In such an embodiment, an opening or slot 765 in the shroud 760 could be used to access the test specimens. With the opening or slot 765 located in the shroud 760, the O-rings or backup rings can be installed into the mandrel or tubular 410 pocket or groove without applying grease. The lack of grease, in this embodiment, allows for maximum exposure of the material test specimen to the wellbore environment. In yet another embodiment, the shroud 760 is configured to move linearly and rotate with respect to the mandrel or tubular 410 to expose the test specimens. In such an embodiment, the shroud 760 and the mandrel or tubular 410 could have a threaded engagement to provide the relative linear and rotational movement. Turning to FIG. 7B, illustrated is a zoomed in view of the material test sub 700 of FIG. 7A.

Figure 8:
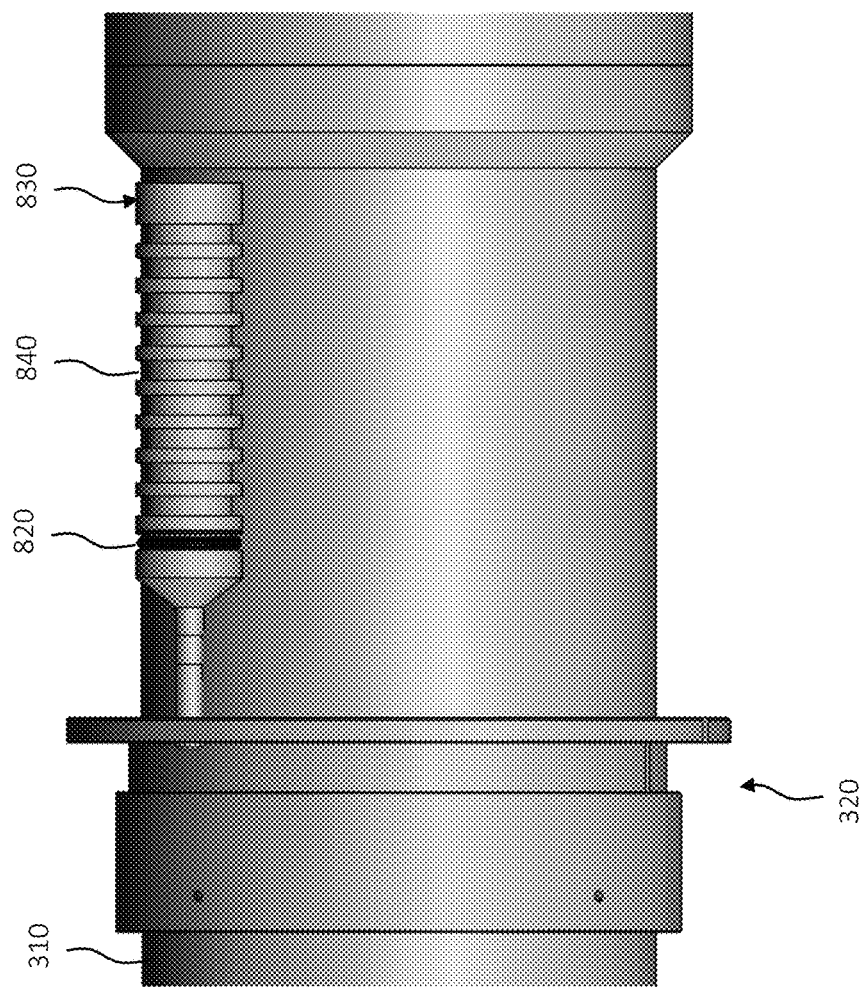
FIG. 8 illustrates a material test sub designed, manufactured, and operated according to one or more other embodiments of the disclosure.

Turning to FIG. 8, illustrated is another embodiment of a material test sub 800 designed, manufactured and operated according to one embodiment of the disclosure. The material test sub 800 is similar in certain respects to the material test sub 300a of FIG. 3A. Accordingly, like reference numbers have been used to indicate similar features. The material test sub 800 differs, for the most part, from the material test sub 300a, in that the material test sub 800 employs a spool 830, having one or more grooves 840 configured to position one or more O-rings and/or backup rings 820. In at least one embodiment, the spool 830 and/or the grooves 840 are machined to carry different sizes of O-rings and/or backup rings 820, as well as provide different stress levels to the O-rings and/or backup rings 820. In another embodiment, the spool 830 and/or the grooves 840 are machined to carry the same sizes of O-rings and/or backup rings 820. Furthermore, multiple spools 830 may be coupled radially about the material test sub assembly 320, as well as multiple material test sub-assemblies 320 may be linearly coupled along the tubular or mandrel 310.

Figure 9A:
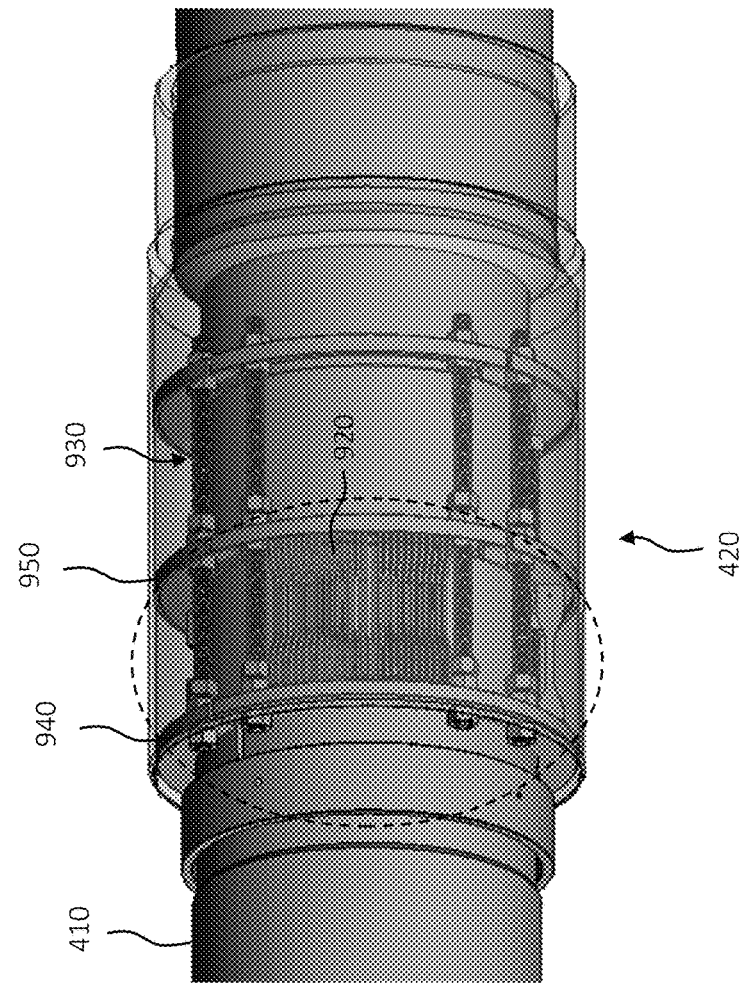

Turning to FIG. 9A, illustrated is another embodiment of a material test sub 900 designed, manufactured and operated according to one embodiment of the disclosure. The material test sub 900 is similar in certain respects to the material test sub 400 of FIG. 4A. Accordingly, like reference numbers has been used to indicate similar features. The material test sub 900 differs, for the most part, from the material test sub 400, in that the material test sub 900 employs a vertical rack arrangement 930 configured to carry elastomeric and/or non-elastomeric test specimens 920. The vertical rack arrangement 930 may include a split flange 940 and segment carrier 950 that allows space to be optimized while still ensuring each test specimen 920 is exposed to the necessary downhole conditions. In this embodiment, the test specimens 920 are strips of material (e.g., dumbbell shaped strips), as opposed to bars or donut shaped test specimens. The test specimens 920 are retained in place axially by securing with wire around a threaded bar. A length between the racks can be varied to allow different length test specimens to be carried in the same plane. Again, in one or more embodiments this feature may be shrouded and modular. Turning to FIG. 9B, illustrated is a zoomed in view of the material test sub 900 of FIG. 9A.

Aspects disclosed herein include:
A. A downhole material test sub assembly, the downhole material test sub assembly including: 1) a flange for coupling to a mandrel; and 2) one or more retainer assemblies coupled to the flange, the one or more retainer assemblies configured to accept a test specimen for running within a wellbore on the mandrel.
B. A well system, the well system including: 1) a wellbore extending into a subterranean formation; 2) a mandrel located in the wellbore; and 3) a downhole material test sub assembly coupled to the mandrel, the downhole material test assembly including: a) a flange coupled to the mandrel; b) one or more retainer assemblies coupled to the flange; and c) a test specimen accepted within the one or more retainer assemblies.
C. A method, the method including: 1) placing a downhole material test sub assembly around a mandrel, the downhole material test assembly including: a) a flange coupled to the mandrel; b) one or more retainer assemblies coupled to the flange; and c) a test specimen accepted within the one or more retainer assemblies; 2) placing the downhole material test assembly having the test specimen within a wellbore extending into a subterranean formation.
D. A downhole material test sub assembly, the downhole material test sub assembly including: 1) a mandrel; and 2) one or more grooves or pockets located in an outer surface of the mandrel, the one or more grooves or pockets configured to accept a test specimen for running within a wellbore on the mandrel.
E. A well system, the well system including: 1) a wellbore extending into a subterranean formation; 2) a tubular located in the wellbore; and 3) a downhole material test sub assembly coupled to the tubular, the downhole material test assembly including: a) a mandrel; b) one or more grooves or pockets located in an outer surface of the mandrel, the one or more grooves or pockets configured to accept a test specimen for running within a wellbore on the mandrel; and c) a test specimen accepted within the one or more grooves or pockets.
F. A method, the method including: 1) coupling a downhole material test sub assembly to a tubular, the downhole material test assembly including: a) a mandrel; b) one or more grooves or pockets located in an outer surface of the mandrel, the one or more grooves or pockets configured to accept a test specimen for running within a wellbore on the mandrel; and c) a test specimen accepted within the one or more grooves or pockets; 2) placing the tubular and the downhole material test assembly having the test specimen within a wellbore extending into a subterranean formation.

Aspects A, B, C, D, E and F may have one or more of the following additional elements in combination: Element 1: wherein the one or more retainer assemblies each include one or more retainer rings, wherein each retainer ring is configured to accept a single test specimen for running within the wellbore. Element 2: further including a single metallic test specimen positioned within ones of the one or more retainer rings. Element 3: wherein the single metallic test specimen is positioned in tension within ones of the one or more retainer rings. Element 4: wherein the single metallic test specimen is positioned in compression within ones of the one or more retainer rings. Element 5: wherein the single metallic test specimen has one or more threaded ends. Element 6: wherein the one or more retainer rings each include a retainer nut for keeping the single metallic test specimen within the one or more retainer rings when the single metallic test specimen breaks. Element 7: further including two or more retainer assemblies radially coupled about the flange. Element 8: wherein at least one of the one or more retainer assemblies includes a first layer configured to accept a first test specimen and a second layer configured to accept a second test specimen. Element 9: further including a shroud at least partially covering the one or more retainer assemblies. Element 10: wherein the shroud is configured linearly slide to expose the one or more retainer assemblies. Element 11: wherein the shroud is configured to rotate to expose the one or more retainer assemblies. Element 12: wherein the shroud includes an opening for accessing the one or more retainer assemblies. Element 13: wherein the one or more retainer assemblies are one or more donut assemblies. Element 14: wherein the one or more donut assemblies each include donut shaped grooves for accepting a non-metallic test specimen. Element 15: wherein the donut shaped grooves hold the non-metallic test specimen in tension. Element 16: wherein the donut shaped grooves hold the non-metallic test specimen in compression. Element 17: wherein the non-metallic test specimen is an O-ring or backup ring. Element 18: wherein the one or more retainer assemblies are one or more spools configured to accept the test specimen. Element 19: wherein each of the one or more spools is configured to accept multiple test specimens. Element 20: wherein at least one of the one or more retainer assemblies is a vertical rack arrangement configured to accept multiple test specimens. Element 21: wherein the vertical rack arrangement includes a split flange and a segment carrier. Element 22: wherein the multiple test specimens are multiple strips of test material radially space about the split flange. Element 23: wherein the multiple strips are multiple strips of elastomeric or non-elastomeric test specimens. Element 24: wherein the downhole material test sub is a first downhole material test sub assembly, and further including a second downhole material test sub assembly coupled to the mandrel, the second downhole material test assembly including: a second flange coupled to the mandrel; one or more second retainer assemblies coupled to the second flange; and a second test specimen accepted within the one or more second retainer assemblies. Element 25: wherein placing the downhole material test assembly includes placing the downhole material test assembly at a location within the wellbore having a desired temperature or pressure. Element 26: further including allowing the downhole material test assembly having the test specimen to remain within the wellbore for a period of time. Element 27: further including removing the downhole material test assembly having the test specimen from the wellbore. Element 28: further including performance testing the test specimen having been removed from the wellbore. Element 29: wherein the one or more grooves or pockets are one or more circular grooves or pockets. Element 30: wherein the one or more grooves or pockets are one or more grooves configured to hold the test specimen in tension. Element 31: wherein the one or more grooves or pockets are one or more pockets configured to hold the test specimen in compression. Element 32: further including a single non-metallic test specimen located in each of the one or more grooves or pockets. Element 33: wherein the single non-metallic test specimen is an O-ring or backup ring. Element 34: further including a shroud at least partially covering the one or more grooves or pockets. Element 35: wherein the shroud is configured linearly slide to expose the one or more grooves or pockets. Element 36: wherein the shroud is configured to rotate to expose the one or more grooves or pockets. Element 37: wherein the shroud is configured to linearly slide to expose the one or more grooves or pockets. Element 38: wherein the shroud includes an opening for accessing the one or more grooves or pockets. Element 39: further including one or more grooves and pockets located in the outer surface of the mandrel. Element 40: further including multiple layers of grooves or pockets located along the mandrel. Element 41: wherein the grooves or pockets in each layer are radially spaced about the mandrel. Element 42: wherein the grooves or pockets in one layer are rotationally offset from the grooves or pockets in an adjacent layer. Element 43: wherein the mandrel is coupled to production tubing. Element 44: wherein the mandrel is production tubing.

Those skilled in the art to which this application relates will appreciate that other and further additions, deletions, substitutions, and modifications may be made to the described embodiments.

What is claimed is:

1. A downhole material test sub assembly, comprising:
   a mandrel having an outer surface; and
   one or more grooves or pockets, wherein the one or more grooves or pockets comprise shaped depressions in the outer surface of the mandrel, the one or more grooves or pockets configured to accept a test specimen for running within a wellbore on the mandrel, wherein the one or more grooves or pockets are shaped to hold the test specimen in tension or compression.

2. The downhole material test sub assembly as recited in claim 1, wherein the one or more grooves or pockets are one or more circular grooves or pockets.

3. The downhole material test sub assembly as recited in claim 1, wherein the one or more grooves or pockets are one or more grooves configured to at least partially employ friction to hold the test specimen in tension.

4. The downhole material test sub assembly as recited in claim 1, wherein the one or more grooves or pockets are one or more pockets configured to at least partially employ friction to hold the test specimen in compression.

5. The downhole material test sub assembly as recited in claim 1, further including a single non-metallic test specimen located in each of the one or more grooves or pockets.

6. The downhole material test sub assembly as recited in claim 5, wherein the single non-metallic test specimen is an O-ring or backup ring.

7. The downhole material test sub assembly as recited in claim 1, further including a shroud at least partially covering the one or more grooves or pockets.

8. The downhole material test sub assembly as recited in claim 7, wherein the shroud is configured to linearly slide to expose the one or more grooves or pockets.

9. The downhole material test sub assembly as recited in claim 7, wherein the shroud is configured to rotate to expose the one or more grooves or pockets.

10. The downhole material test sub assembly as recited in claim 9, wherein the shroud is configured to linearly move to expose the one or more grooves or pockets.

11. The downhole material test sub assembly as recited in claim 9, wherein the shroud includes an opening for accessing the one or more grooves or pockets.

12. The downhole material test sub assembly as recited in claim 1, further including one or more grooves and one or more pockets located in the outer surface of the mandrel.

13. The downhole material test sub assembly as recited in claim 1, further including multiple layers of grooves or pockets located along the mandrel.

14. The downhole material test sub assembly as recited in claim 13, wherein the grooves or pockets in each layer are radially spaced about the mandrel.

15. The downhole material test sub assembly as recited in claim 14, wherein the grooves or pockets in one layer are rotationally offset from the grooves or pockets in an adjacent layer.

16. The downhole material test sub assembly as recited in claim 1, wherein the mandrel is coupled to production tubing.

17. The downhole material test sub assembly as recited in claim 1, wherein the mandrel is production tubing.

18. A well system, comprising:
    a wellbore extending into a subterranean formation;
    a tubular located in the wellbore; and
    a downhole material test sub assembly coupled to the tubular, the downhole material test assembly including:
    a mandrel having an outer surface;
    one or more grooves or pockets, wherein the one or more grooves or pockets comprise shaped depressions in the outer surface of the mandrel, the one or more grooves or pockets configured to accept a test specimen for running within a wellbore on the mandrel, wherein the one or more grooves or pockets are shaped to hold the test specimen in tension or compression; and
    a test specimen accepted within the one or more grooves or pockets.

19. The well system as recited in claim 18, wherein the test specimen is an O-ring or backup ring.

20. The well system as recited in claim 18, further including a shroud at least partially covering the one or more grooves or pockets.

21. The well system as recited in claim 20, wherein the shroud is configured linearly slide to expose the one or more grooves or pockets.

22. The well system as recited in claim 20, wherein the shroud is configured to rotate to expose the one or more grooves or pockets.

23. The well system as recited in claim 22, wherein the shroud is configured to linearly move to expose the one or more grooves or pockets.

24. The well system as recited in claim 22, wherein the shroud includes an opening for accessing the one or more grooves or pockets.

25. A method, comprising:
coupling a downhole material test sub assembly to a tubular, the downhole material test assembly including:
a mandrel having an outer surface;
one or more grooves or pockets, wherein the one or more grooves or pockets comprise shaped depressions in the outer surface of the mandrel, the one or more grooves or pockets configured to accept a test specimen for running within a wellbore on the mandrel, wherein the one or more grooves or pockets are shaped to hold the test specimen in tension or compression; and
a test specimen accepted within the one or more grooves or pockets; and
placing the tubular and the downhole material test assembly having the test specimen within a wellbore extending into a subterranean formation.

26. The method as recited in claim 25, wherein placing the downhole material test assembly includes placing the downhole material test assembly at a location within the wellbore having a desired temperature or pressure.

27. The method as recited in claim 26, further including allowing the downhole material test assembly having the test specimen to remain within the wellbore for a period of time.

28. The method as recited in claim 27, further including removing the downhole material test assembly having the test specimen from the wellbore.

29. The method as recited in claim 28, further including performance testing the test specimen having been removed from the wellbore.

* * * * *